United States Patent
Beard et al.

(10) Patent No.: US 6,831,188 B1
(45) Date of Patent: Dec. 14, 2004

(54) DIHYDROCARBYLAMINO METAL COMPOUNDS

(75) Inventors: William R. Beard, Baton Rouge, LA (US); Robin L. Neil, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 10/209,714

(22) Filed: Jul. 31, 2002

(51) Int. Cl.$^7$ .............................. C07F 7/28; C23C 16/00
(52) U.S. Cl. ......................... 556/51; 427/587; 427/593; 423/409
(58) Field of Search .......................... 556/51; 427/587, 427/593; 423/409

(56) References Cited

U.S. PATENT DOCUMENTS

| | | | |
|---|---|---|---|
| 2,579,413 A | * 12/1951 | Boyd | .......................... 556/51 |
| 3,370,041 A | 2/1968 | Kornicker et al. | ............ 260/67 |
| 5,178,911 A | 1/1993 | Gordon et al. | ........... 427/255.2 |
| 5,417,823 A | 5/1995 | Narula et al. | ............ 204/157.4 |
| 6,020,444 A | 2/2000 | Riedel et al. | ................ 526/170 |
| 6,080,446 A | 6/2000 | Tobe et al. | ........... 427/255.394 |

FOREIGN PATENT DOCUMENTS

DE          269387       6/1989

OTHER PUBLICATIONS

Antler, Morton et al; "Donor–Acceptor Bonding. VI. The Reactions of Trimethylamine, Dimethyl–amine, Monomethylamine, and Ammonia with Titanium Tetrachloride and of Trimethylamine with Titanium Trichloride"; J. Am. Chem. Soc.; vol. 77; 1955 pp. 5250–5253.

Bradley, D.C. et al.; "Metallo–organic Compounds Containing Metal–Nitrogen bonds. Part 1. Some Dialkylamino derivatives of Titanium and Zirconium"; J. Chem. Soc.; 1960; pp. 3857–3861.

Bürger, Von Hans et al.; "Die Synthese von Diorganylamino–titanchloriden über trimethylsilylamine"; Z. Anorg. Allg. Chem.; 365; 1969; pp. 243–254.

Bürger, Hans et al.; Titanium–nitrogen Compounds: VII*. Preparation, IR, Raman, and 1H–CMR spectra of Tris(dialkylamino)titanium alkylene; J. Organometal. Chem. 20, 1969; pp. 129–139. (selected portion translated 2 pages).

Chandler, John A. et al.; "The Reaction of Titanium Tetrafluoride with Di–η–propylamine"; Inorganic Chemistry; vol. 1; No. 1; Feb. 1962; pp. 65–69.

Chandler, John A. et al.; "The Reaction of Titanium Tetrafluoride with Diisopropylamine, Diethyl–amine, Pyridine, and Triethylamine"; Inorganic Chemistry; vol. 1; No. 2; May 1962; pp. 356–358.

Chemical Abstract, # 84101, Chumaevskii, N.A. et al.; "Reactions of Acetonitrile with Titanium Tetrachloride in the Presence of Primary, Secondary and Tertiary Amines"; Koord. Khim; 1991; No. 17; vol. 4; pp. 463–466. (2 pages).

Cowdell, R.T. et al.; "Amine Compounds of the Transition Metals. Part VI. The Reaction of Titanium(iv) Chloride with Some Aliphatic Amines"; J. Chem. Soc.; 1960 pp. 2522–2526.

Irigoyen, Ana Maria et al.; "Synthesis and Characterisation of Chlorobis(dialkylamido) and alkylbis(di–alkylamido) derivitives of [$\eta^5$–C$_5$Me$_5$)MCl$_3$](M= Ti,Zr)" J. Org. Chem.; vol. 494; 1995; p. 255–259.

Prasad, Sarju et al.; "Amino Derivitives of Titanium Tetrabromide. Part I."; Jour. Indian Chem. Soc.; vol. 33; No. 11; 1956; pp. 838–840.

Prasad, Sarju et al.; "Amino Derivitives of Titanium Tetrabromide. Part II. "; Jour. Indian Chem. Soc.; vol. 34; No. 6; 1957; pp. 452–456.

Prasad, Sarju et al.; "Amino Derivitives of Titanium Tetrabromide. Part III."; Jour. Indian Chem. Soc.; vol. 34; No. 10; 1957; pp. 749–752.

Reetz, M.T. et al.; "An Economical Large–Scale Synthesis of Titanium Tetrakis[diethylamide] and Chlorotitanium Tris [diethylamid]"; Synthesis; vol. 7; 1983; p. 540.

Steinborn' Dirk et al. "An Efficient Synthesis of Titanium and Zirconium Tetrakis(diethylamide)"; Synthesis; vol. 4; 1989; p. 304.

* cited by examiner

*Primary Examiner*—Porfirio Nazario-Gonzalez
(74) *Attorney, Agent, or Firm*—Edgar E. Spielman, Jr.

(57) ABSTRACT

This invention provides a process of preparing dihydrocarbylamido metal compounds. This process comprises bringing together, in a liquid reaction medium, at least one metal halide, MX$_4$, where M is titanium, zirconium, or hafnium, and X is a halogen atom, with at least one dihydrocarbylamine, such that a mixture of (i) halometal amides in which the atom ratio of halogen to metal is greater than about 0.1 and less than about 2, and (ii) dihydrocarbylamine hydrohalide is produced. Then (i) and (ii) are separated from each other, and (i) is brought together with an alkali metal amide, ANR$_2$, where A is an alkali metal, and R is a hydrocarbyl group, in a liquid medium, to produce a product comprised of substantially halogen-free dihydrocarbylamido metal compound.

This invention further provides for purifying dihydrocarbylamido metal compounds by contact with a nitrile.

54 Claims, No Drawings

DIHYDROCARBYLAMINO METAL COMPOUNDS

TECHNICAL FIELD

This invention relates to the preparation and purification of dialkylamino metal compounds.

GLOSSARY

As used herein, the terms "dihydrocarbylamino metal compound" and "dihydrocarbylamido metal compound" are synonymous. Such compounds are also referred to as metal amides. Also, as used herein, the term "halometal amide" means a metal compound that contains both halide and dihydrocarbylamino ligands.

BACKGROUND

Metal amides, particularly homoleptic dialkylamino metal compounds, are useful as precursor compounds for chemical vapor deposition. See in this connection U.S. Pat. Nos. 5,178,911; 5,417,823; and 6,080,446. Such metal amides are also useful in the synthesis of polymerization catalysts; see for example U.S. Pat. No. 6,020,444. The usual method employed for making metal amides is to react a metal halide with lithium amide, and to purify the product via vacuum distillation. See D. C. Bradley and I. M. Thomas, *Proc. Chem. Soc.*, 1959 225–226, D. C. Bradley and I. M. Thomas, *J. Chem. Soc.*, 1960 3857–3861; and M. T. Reetz et al., *Synthesis*, 1983 7 540. Most often, the lithium amide is made from butyl lithium or lithium, expensive reagents, and the corresponding amine. When a lithium amide is used, the solid lithium halide by-product often consists of very small particles that are difficult to remove, especially at large scales. An alternative method employs halomagnesium amide in place of lithium amide; see D. Steinborn et al., *Synthesis*, 1989 4 304, and DD 269387 A1. After either synthetic procedure, the metal amide is usually purified by vacuum distillation. Many metal amides decompose at the distillation temperature, causing yield losses.

Also known in the art are metal complexes having both halide and dialkylamino ligands. Such compounds can be made by ligand exchange between, for example, $TiCl_4$ and $Ti[N(CH_3)_2]_4$, or by the use of less than four moles of $LiN(CH_3)_2$ when the reactant is $TiCl_4$, see U.S. Pat. No. 3,370,041. Another approach, described by R. T. Cowdell and G. W. A. Fowles, *J. Chem. Soc.*, 1960 2522–2526, is reacting $TiCl_4$ with four moles of dialkylamine, which results in the replacement of only one chlorine ligand. The halide ligands on these halometal amide compounds have been replaced with organic groups; for example, $TiBr[N(CH_3)_2]_3$ is reacted with methyllithium; see H. Burger and H. J. Neese, *J. Organometallic Chem.*, 1969 20 129–139.

It has been reported that reaction occurs when dialkylamino metal compounds are contacted with acetonitrile. See D. C. Bradley and M. C. Ganorkar, *Chem. Ind.*, 1968 1521–1522, and D. C. Bradley and M. Ahmed, *Polyhedron*, 1983 2 87. The reaction of $TiCl_4$ with acetonitrile in the presence of amines has been described by N. A. Chumaevskii et al., *Koord. Khim.*, 1991 17 463–466 (*Chemical Abstracts*, 115:84101n, 1991).

It would be advantageous to find a better synthetic route to dialkylamino metal compounds. A more effective purification method for these compounds is also desirable.

SUMMARY OF THE INVENTION

This invention is deemed to enable achievement of the above advantages.

The process of this invention for making the dihydrocarbylamino metal compound has the advantage that the amount of alkali metal amide used decreases from four moles to less than about two moles, and the amount of alkali metal halide by-product produced is correspondingly reduced. Additionally, the dihydrocarbylamino metal compound does not have to be purified via distillation.

An embodiment of this invention is a process of preparing dihydrocarbylamido metal compounds. This process comprises bringing together, in a liquid reaction medium, at least one metal halide, $MX_4$, where M is titanium, zirconium, or hafnium, and X is a halogen atom, with at least one dihydrocarbylamine, such that a mixture of (i) halometal amides in which the atom ratio of halogen to metal is greater than about 0.1 and less than about 2, and (ii) dihydrocarbylamine hydrohalide is produced. Then (i) and (ii) are separated from each other, and (i) is brought together with an alkali metal amide, $ANR_2$, where A is an alkali metal, and R is a hydrocarbyl group, in a liquid medium, to produce a product comprised of substantially halogen-free dihydrocarbylamido metal compound.

Another embodiment of this invention is also a process of preparing dihydrocarbylamido metal compounds. This process comprises reacting at least one alkali metal dihydrocarbylamide, $ANR_2$, where A is an alkali metal, and R is an hydrocarbyl group, with at least one halometal amide in which the atom ratio of halogen to metal is greater than about 0.1 and less than about 2, where the metal of the halometal amide is titanium, zirconium, or hafnium, to produce a product comprised of substantially halogen-free dihydrocarbylamido metal compound.

Still another embodiment of this invention is the discovery that dihydrocarbylamido metal compounds can be purified by contact with a nitrile. Thus, this purification step can be performed in connection with the other embodiments of this invention.

Other embodiments and features of this invention will become still further apparent from the ensuing description and appended claims.

FURTHER DETAILED DESCRIPTION

The metal halides used in invention have the formula $MX_4$, where M is titanium, zirconium, or hafnium, and X is a halogen atom. The halogen atom can be a fluorine, chlorine, bromine, or iodine atom. Normally and preferably, all four halogen atoms are the same, as such reagents are readily available commercially. Thus, suitable metal halides include titanium tetrafluoride, titanium tetrachloride, titanium tetrabromide, titanium iodide, zirconium tetrafluoride, zirconium tetrachloride, zirconium tetrabromide, zirconium iodide, hafnium tetrafluoride, hafnium tetrachloride, hafnium tetrabromide, and hafnium iodide. Preferably, the metal is titanium or zirconium, more preferred as the metal is titanium. The halogen atom is preferably a chlorine, bromine, or iodine atom, more preferably, the halogen atom is a chlorine or bromine atom. Highly preferred metal halides for use in this invention thus are titanium tetrachloride, titanium tetrabromide, zirconium tetrachloride, and zirconium tetrabromide.

Dihydrocarbylamines that can be used in this invention have hydrocarbyl groups that may be the same or different, and each hydrocarbyl group has, independently, from 1 to about 12 carbon atoms. Preferably, each hydrocarbyl group has from 1 to about 5 carbon atoms, preferred dihydrocarbylamines are those in which the hydrocarbyl groups are the same. Examples of dihydrocarbylamines that can be used include, but are not limited to, dimethylamine, dimethylamine, ethylmethylamine, ethyl-n-propylamine, methyl-n-propyl-amine, di-n-propylamine, diisopropylamine, methylisopropylamine, ethylisopropylamine, n-butylethylamine, di-n-butylamine, diisobutylamine, isobutylpropylamine, dicyclobutylamine, (cyclobutyl)(methyl)amine, dipentylamine, methylpentylamine, (n-propyl)(pentyl)amine, dicyclopentylamine, (cyclopentyl)pentylamine, dihexylamine, ethylhexylamine, dicyclohexylamine, (isopropyl)(cyclohexyl)amine, diheptylamine, dicycloheptylamine, dioctylamine, n-butyloctylamine, methyloctylamine, dicyclooctylamine, dinonylamine, ethylnonylamine, isobutyldecylamine, didecylamine, (methyl)(phenyl)amine, (ethyl)(phenyl)amine, diphenylamine, bis(biphenyl)amine, ditolylamine, dixylylamine, di(ethylphenyl)amine, di(isopropylphenyl)amine, (n-propyl)(tolyl)amine, dinaphthylamine, (cyclohexyl)(naphthyl)amine, pyrrolidine, pyrrole, and piperidine. Preferred dihydrocarbyl-amines are dimethylamine, diethylamine, and di-n-propylamine, more preferred are dimethylamine and diethylamine. Mixtures of two or more dihydrocarbylamines may be used; preferably, a single dihydrocarbylamine is used.

For the bringing together of the metal halide and the dihydrocarbylamine, the liquid reaction medium can be comprised of one or more alkanes, aromatic hydrocarbons, hydrocarbylaromatic hydrocarbons, ethers, or mixtures thereof, that are liquid at the conditions at which the addition is conducted. When the dihydrocarbylamine being used is a liquid, the process can be done in the absence of additional component(s). Suitable components of the liquid reaction medium include pentane, cyclpentane, hexane, cyclohexane, methylcyclohexane, cyclohexene, heptane, cycloheptane, octane, isooctane, cyclooctane, cyclooctadiene, nonane, benzene, toluene, xylene, diethyl ether, di-n-propyl ether, ethyl-n-propyl ether, diisopropyl ether, tert-butyl ethyl ether, di-n-butyl ether, diheptyl ether, oxetane, tetrahydrofuran, methyltetrahydrofuran, 1,4-dioxane, 1,3-dioxolane, cyclohexylmethyl ether, and the like. A preferred type of component of the liquid reaction medium are alkanes. Preferred alkanes are pentane, hexane, cyclohexane, heptane, octane, and isooctane; more preferred are hexane, cyclohexane, and heptane. The most preferred liquid reaction medium comprises hexane and/or cyclohexane.

The alkali metal amide has the formula $ANR_2$, where A is an alkali metal, and R is an hydrocarbyl group. The alkali metal is preferably lithium, sodium, or potassium; more preferable are lithium and sodium; most preferred is lithium. The two hydrocarbyl groups of the amide may be the same or different, and are as described above for the dihydrocarbylamines. Suitable alkali metal amides include, for example, lithium dimethylamide, sodium dimethylamide, potassium dimethylamide, lithium ethylmethylamide, sodium ethylmethylamide, potassium ethylmethylamide, lithium diethylamide, sodium diethylamide, potassium diethylamide, lithium di-n-propylamide, sodium di-n-propylamide, potassium di-n-propylamide, lithium diisopropylamide, sodium ethyl-n-propylamide, potassium methylisopropylamide, lithium di-n-butylamide, sodium diisobutylamide, potassium n-butylethylamide, lithium dicyclobutylamide, sodium dipentylamide, potassium methylpentylamide, lithium dicyclopentylamide, sodium dihexylamide, potassium ethylhexylamide, lithium dicyclohexylamide, sodium dihepylamide, potassium dioctylamide, lithium methyloctylamide, sodium dicyclooctylamide, potassium dinonylamide, lithium ethylnonylamine, sodium didecylamine, potassium (methyl)(phenyl)amide, lithium (ethyl)(phenyl)amide, sodium diphenylamide, potassium ditolylamide, lithium (n-propyl)(tolyl)amide, sodium dinaphthylamide, potassium (cyclohexyl)(naphthyl)amide, lithium-pyrrolidine salt, sodium-pyrrole salt, and potassium-piperidine salt. Preferred alkali metal amides are lithium dimethylamide, sodium dimethylamide, lithium diethylamide, sodium diethylamide, lithium dipropylamide, and sodium dipropylamide. Most preferred are lithium dimethylamide and lithium diethylamide.

When it is said that the alkali metal amide corresponds to the dihydrocarbylamine, it is meant that the amide has the same two hydrocarbyl groups as the amide ligands of the halometal amide. Using an alkali metal amide that has hydrocarbyl groups which correspond to those of the halometal amide is preferred.

When there will be solvent as part of the liquid reaction medium, the amine is normally mixed with such solvent prior to being brought together with the metal halide. The metal halide may be brought together with the amine as a solid, or in a mixture with a suitable solvent. Such solvents are those described above for used as components of the liquid reaction medium. When the metal halide is in a mixture with a solvent, it is preferred that the metal halide is soluble in that solvent. Preferably, the metal halide is a solution or slurry in a suitable solvent; most preferable is to use the metal halide as a solution in a suitable solvent. It is also preferred that some liquid is present when the process is finished to prevent the slurry from becoming too viscous to transfer easily.

Without wishing to be bound by theory, it is believed that the metal halide must be in the presence of a locally high concentration of dihydrocarbylamine for the process to be successful. When the metal halide is present in higher concentration relative to the amine, trihalometal amide products and/or tars are usually produced. Mixing during the bringing together of the metal halide and the dihydrocarbylamine is important to avoid locally high concentrations of metal halide (and thus locally low concentrations of amine). Generally, stirring of the reaction mixture both during and after the bringing together of the metal halide and the dihydrocarbylamine is vigorous. If the reaction mixture is not stirred after the bringing together, it usually becomes a very viscous slurry which is not easy to transfer. Typical methods of bringing the amine and metal halide together include cofeeding (where the feed of amine is such that a locally high concentration of amine is present relative to the metal halide) and addition of the metal halide to a vessel containing the dihydrocarbylamine.

At least about a slight molar excess of dihydrocarbylamine relative to metal halide preferably is used in the process. An equimolar amount is about one mole of dihydrocarbylamine for each mole of halide ligands; thus, four moles of dihydrocarbylamine for each mole of $MX_4$ is considered to be the equimolar amount.

During the bringing together of the metal halide and the dihydrocarbylamine, the reaction temperature is preferably kept low, cooling is often necessary to maintain the low temperature because the reaction is exothermic. Preferably, the temperatures are no higher than about 40° C., more preferably, the temperature is no higher than about 20° C. The temperature is most preferably no higher than about 5° C. Allowing the temperature to rise above about 60° C. is believed to decrease the yield of the desired product by increasing the rate of the side reactions.

In the practice of this invention, the halometal amides produced have an atom ratio of halogen to metal greater than about 0.1 and less than about 2. The process typically produces mixtures of monohalometal amides and dihalometal amides, with a varying ratio of monohalometal amide to dihalometal amide. The atom ratio becomes lower as more monohalometal amide is produced relative to dihalometal amide. When the halometal amide is made as an intermediate compound before making a dihydrocarbylamido metal compound, the process is preferably optimized to produce halometal amides with lower atom ratios of halogen to metal. This minimizes the amount of alkali metal amide needed to make the dihydrocarbylamido metal compound.

Halometal amides having an atom ratio of halogen to metal greater than about 0.1 and less than about 2, however made, may be brought together with alkali metal amides to produce a substantially halogen-free dihydrocarbylamido metal compound. By using the phrase "substantially halogen-free," it is recognized that the dihydrocarbylamido metal compound, which is desirably halogen-free, may contain small amounts of adventitious halogen.

Normally, the halometal amide and alkali metal amide are brought together in a liquid medium in which the alkali metal amide is soluble, although it is not necessary for the alkali metal amide to be dissolved for the process to work. It is preferred to use a liquid medium in which the alkali metal amide is soluble. The halometal amide may be in the form of a solvent-free liquid, a slurry, or a solution when it is brought together with the alkali metal amide. When the halometal amide is a liquid, it need not be mixed with another component to form a solution before being brought together with the alkali metal amide. This process is preferably performed at temperatures in the range of about $-15°$ C. to about 40° C., to keep the temperature in this range usually requires cooling because the reaction is exothermic. Preferably, the temperature is in the range of about 0° C. to about 20° C. Stirring during the bringing together of the halometal amide with the alkali metal amide is typically vigorous.

Means for solubilizing alkali metal amides generally involve including a Lewis base in the liquid medium. Such Lewis base may be added before, during, and/or after the halometal amide and the alkali metal amide are brought together. Acceptable Lewis bases are those that solubilize the alkali metal amide and do not adversely affect the process, e.g., by reacting with the halometal amide. Mixtures of Lewis bases may be employed, but use of a single Lewis base is preferred. Suitable types of Lewis bases include, for example, trialkylamines and ethers. Trialkylamines that can be used include trimethylamine, ethyldimethylamine, triethylamine, tri-n-propylamine, triisopropylamine, tri-n-butylamine, tricyclohexylamine, and the like. A preferred trialkylamine is triethylamine. Suitable ethers include diethyl ether, di-n-propyl ether, ethyl-n-propyl ether, diisopropyl ether, tert-butyl ethyl ether, di-n-butyl ether, diheptyl ether, oxetane, tetrahydrofuran, methyltetrahydrofuran, cyclohexylmethyl ether, and the like. Preferred ethers are diethyl ether, tetrahydrofuran, and methyltetrahydrofuran. Ethers are a preferred type of Lewis base. The use of enough Lewis base to dissolve the alkali metal amide is preferred, a greater amount of Lewis base is not expected to harm the process. For an ether, it is preferred to have at least about one mole of ether per mole of alkali metal cation present in the liquid medium.

It has been discovered that dihydrocarbylamido metal compounds can be purified by contact with a nitrile. Usually, the mixture undergoing treatment contains mostly metal amide, alkali metal halide, and unreacted alkali metal amide. For the nitrile treatment, at least enough nitrile to consume leftover alkali metal amide should be used. Preferably, an excess amount of nitrile is used, because, without wishing to be bound by theory, it is thought that the nitrile also consumes other undesired side products, such as reduced metal species.

The dihydrocarbylamido metal compound can be purified by contact with a nitrile in a number of ways. One preferred manner in which to carry out the nitrile treatment is to perform several nitrile washes of the metal amide product. For these washing procedures, the temperature at which the nitrile treatment is conducted is preferably in the range of about −30° C. to about 40° C. to minimize undesired side reactions, which usually include decomposition of the dihydrocarbylamido metal compound. More preferably, the temperature is in the range of about −30° C. to about 25° C., most preferred is a temperature in the range of about −15° C. to about 0° C. Contact times are normally less than about 36 hours, preferably less than about 6 hours, and most preferably in the range of about 1 to 4 hours on the laboratory scale. Good results at room temperature may be obtained by decreasing the contact time of the nitrile and the dihydrocarbylamino metal compound. However, improved removal of the alkali metal species has been observed at lower temperatures.

Suitable nitriles include acetonitrile, acrylonitrile, propionitrile, glutaronitrile, cyclopropyl cyanide, butyronitrile, isobutyronitrile, 1,4-dicyanobutane, 3-butenonitrile, valeronitrile, 1,5-dicyanopentane, 1,6-dicyanohexane, cyclohexyl cyanide, cycloheptyl cyanide, n-heptyl cyanide, undecyl cyanide, benzonitrile, trimethylbenzonitrile, trimethylacetonitrile, diphenylacetonitrile, diphenylpropionitrile, tolunitrile, dicyanobenzene, benzyl cyanide, methylbenzyl cyanide, cinnamonitrile, poly(acetonitrile), poly(propionitrile), poly(butyronitrile), and polyacrylonitrile. Preferred nitriles are acetonitrile, propionitrile, butyronitrile, and poly(acetonitrile), poly(propionitrile), and poly(butyronitrile), more preferred are acetonitrile, propionitrile, and butyronitrile. The most preferred nitrile in the practice of this invention is acetonitrile.

There are no particular requirements for the result of the nitrile treatment, except that it should render the dihydrocarbylamino metal compound separable from the nitrile-derived products, preferably, the dihydrocarbylamino metal compound is rendered separable from both the nitrile-derived products and other impurities. Upon treatment with nitrile, the impurities typically form solid products which can be separated from a liquid dihydrocarbylamino metal compound or a solution of a dihydrocarbylamino metal compound via filtration. When filtration is not desirable and/or feasible, it may be possible to separate the nitrile-derived products and other impurities from the dihydrocarbylamino metal compound by centrifugation or by selective absorption of either the dihydrocarbylamino metal compound or its impurities on a solid material such as silica, alumina, titania, or montmorillonite.

The following Examples are presented to illustrate the practice of, and advantages made possible by, this invention. These Examples are not intended to limit, and should not be construed as limiting, the scope of this invention to the particular operations or conditions described therein.

EXAMPLE 1

The reactor, which was installed in a nitrogen-purged glove box, consisted of a 3-liter round-bottomed flask jacketed with a 5-liter round-bottomed flask. It was equipped with a 113-mm-diameter stainless steel stirring blade driven by an overhead stirrer, and its jacket temperature was controlled by a recirculating heating/cooling bath. For this Example, the bath was set at −10° C. The tubes through which materials were introduced to the reactor were made of polytetrafluoroethylene (PTFE).

The reactor was charged with diethylamine (1350 g, 18.5 mol). After cooling to −7.3° C., and while stirring at 198–200 rpm, $TiCl_4$ (248 g, 1.30 mol) was fed sub-surface as a 50 wt % solution in hexanes over about 200 minutes, during which time the reaction temperature slowly rose to −2.4° C. during the first hour and thereafter was maintained at −2.4 to −1.3° C. The product mixture, which consisted of a thick slurry of white solid in a deep-red liquid, was then vacuum filtered through a medium porosity glass frit. Hexane was used as a wash solvent, and the hexane-soluble components, which included $ClTi(NEt_2)_3$ and $Cl_2Ti(NEt_2)_2$, were recovered in the filtrate (mass: 2234 g). The composition of the filtrate is summarized in Table 1. The partially dried $H_2NEt_2Cl$ filter cake was off-white and weighed 422 g.

EXAMPLE 2

The procedure of Example 1 was repeated, with the differences as follows. The diethylamine (1456 g, 19.68 mol) was cooled to −7.0° C., and then $TiCl_4$ (245 g, 1.29 mol) was fed as a 50 wt % solution over about 220 minutes while stirring at 200–205 rpm. The reaction temperature reached −4.6° C. after 75 minutes and +1.1° C. after 161 minutes, and thereafter decreased, reaching −1.6° C. at the end of the $TiCl_4$ addition. The product mixture was filtered using hexane as the wash solvent, yielding 2566 g of filtrate, which had the composition summarized in Table 1.

Table 1. The $H_2NEt_2Cl$ filter cake, when fairly dry, weighed 269 g. The remaining 12% of the reaction mixture stayed in the reactor and was present at the start of Example 5.

EXAMPLE 5

The 3-L reactor, which still contained about 220 g of reaction product slurry from Example 4, was charged with diethylamine (1338 g, 18.3 mol). After cooling to −7.0° C., and while stirring at 338–339 rpm, $TiCl_4$ (223 g, 1.18 mol) was fed sub-surface as a 50 wt % solution in hexane over about 145 minutes; the reaction temperature rose to +5.6° C. About 86% of the reaction product mixture was removed and filtered, using hexane as the wash solvent, yielding 2444 g of filtrate. The composition of the filtrate is summarized in Table 1. The mass of the still-wet $H_2NEt_2Cl$ filter cake was 357 g. The remaining 14% of the reaction mixture stayed in the reactor and was present at the start of Example 6.

EXAMPLE 6

The 3-L reactor, which still contained ~275 g of reaction product slurry from Example 5, was charged with diethylamine (1247 g, 17.0 moles). After cooling to −6.1° C., and while stirring at 341–345 rpm, $TiCl_4$ (248 g, 1.31 mole) was fed sub-surface over 146 minutes; the reaction temperature rose to +4.4° C. The entire reaction mixture was removed and filtered, using hexane as the wash solvent, yielding 2419 g of filtrate, which had the composition summarized in Table 1. The mass of the partially dried $H_2NEt_2Cl$ filter cake was 376 g.

TABLE 1

| Ex | $TiCl_4$ Charged (moles) | Amount of Filtrate (grams) | Composition of Filtrate | | | | Titanium Recovery |
|---|---|---|---|---|---|---|---|
| | | | $TiCl(NEt_2)_3$ (mmol/g) | $TiCl_2(NEt_2)_2$ (mmol/g) | $HNEt_2$ (mmol/g) | Hexane (mmol/g) | |
| 1 | 1.30 | 2234 | 0.290 | 0.271 | 3.43 | 7.06 | 96% |
| 2 | 1.29 | 2566 | 0.286 | 0.195 | 4.17 | 6.22 | 88% |
| 3 | 1.36 | 1836 | 0.389 | 0.320 | 2.82 | 6.93 | ~96% |
| 4 | 1.16 | 1350 | 0.424 | 0.323 | 4.84 | 4.55 | 98% (combined) |
| 5 | 1.18 | 2444 | 0.289 | 0.216 | 4.23 | 5.85 | |
| 6 | 1.31 | 2419 | 0.278g | 0.264 | 3.33 | 6.76 | |

EXAMPLE 3

The procedure of Example 1 was repeated, with the differences as follows. The diethylamine (991.3 g, 13.55 mol) was cooled to −7.4° C., and then $TiCl_4$ (251 g, 1.36 mol) was fed as a 55 wt % solution in hexanes over about 150 minutes, with the reaction temperature reaching a high of +6° C. The product mixture was filtered, using hexane as the wash solvent, yielding 1836 g of filtrate, which had the composition summarized in Table 1.

EXAMPLE 4

The procedure of Example 1 was repeated, with the differences as follows. The diethylamine (1171 g, 16.0 moles) was cooled to −5.7° C. $TiCl_4$ in hexanes (219 g, 1.16 mol) was fed over 126 minutes while stirring at 332–333 rpm, the reaction temperature rose to +5.7° C. About 88% of the product mixture was transferred from the reactor and filtered, using hexane as the wash solvent, yielding 1350 g of filtrate. The composition of the filtrate is summarized in

EXAMPLE 7

The reactor set-up was the same one as that described in Example 1. The reactor was charged with BuLi (64.76 g, 0.927 mmol) and hexane (410 g). After cooling the reactor jacket to −6.8° C., and while stirring, diethylamine (74.38 g, 0.986 mol) was slowly fed over about 60 minutes, during which time the reaction temperature increased to +2.7° C. and white $LiNEt_2$ precipitated. Tetrahydrofuran (THF; 137 g, 1.91 mol) was added, dissolving the LiN $Et_2$.

Chlorotitanium diethylamide solution from Example 1 (1102 g) was fed to the $LiNEt_2$ solution over about 2.5 hours while maintaining the reaction temperature at ~+21° C. and stirring at 99 rpm, whereupon the reaction mixture turned from water-white to yellow, and LiCl precipitated. Residual chlorotitanium diethylamide solution was washed from the supply bottle into the reactor with THF (50 mL). After stirring overnight at room temperature, proton NMR analysis showed that a filtered sample consisted of $HNEt_2$ (14 wt %), hexane (65 wt %), THF (8.6 wt %), and $Ti(NEt_2)_4$ (12 wt %, ~0.62 mol), corresponding to quantitative conversion of chlorotitanium amides to $Ti(NEt_2)_4$.

The reaction product mixture was transferred to a 3-L round-bottomed flask and volatiles were stripped on a Schlenk line while warming the flask with a hot water bath, leaving a non-volatile, orange-amber slurry.

EXAMPLE 8

On the laboratory bench, a 3-liter jacketed reactor equipped with a PTFE-coated magnetic stirring bar was charged with BuLi (64.79 g, 0.928 mol) and hexane (430 g). The reactor's jacket was cooled to about 0° C. and, while stirring, diethylamine (82.1 g, 1.12 mol) was added over about 20 minutes, during which time white $LiNEt_2$ precipitated. After warming to +20° C., THF (140.6 g, 1.95 mol) was added, dissolving the $LiNEt_2$. Chlorotitanium diethylamine solution from Example 1 (1100 g) was then added over about 2 hours while stirring, whereupon the reaction mixture turned from water-white to yellow and LiCl precipitated. The reactor's jacket temperature was briefly increased to +38° C., and then the product mixture was stirred overnight at room temperature, after which volatiles were stripped on a Schlenk line, leaving an orange-amber slurry in the reaction flask.

The stripped reaction product slurries from this Example and Example 7 were combined, hexane (303 g) was added, and the mixture was filtered through a medium porosity glass frit. Volatiles were stripped from the dark-amber filtrate on a Schlenk line while warming with a hot water bath. The resulting dark amber $Ti(NEt_2)_4$ (~385 g) contained 227 ppm Li and ~2000 ppm hexane. The yield of $Ti(NEt_2)_4$ from chlorotitanium diethylamides was ~93%.

EXAMPLE 9

The procedure of Example 7 was repeated, with the differences as follows. The reactor was charged with BuLi (54.66 g, 0.783 mol) and hexane (336 g). After cooling the reactor's jacket about −7° C., diethylamine (61.43 g, 0.840 mol) was fed at variable rates over ~40 minutes while stirring at 50–150 rpm with the reaction temperature reaching a high of +7.2° C. The amount of THF used was 115 g (1.60 mol).

After stirring for ~1 hour at 20° C., a portion of the chlorotitanium diethylamide solution from Example 2 (1098 g) was fed into the $LiNEt_2$ solution over ~135 minutes while stirring at 179 rpm. Residual chlorotitanium diethylamide solution was washed from the supply bottle with hexane (35 mL) and the reaction mixture was stirred at 50 rpm overnight at about 20° C., after which NMR analysis confirmed the presence of $Ti(NEt_2)_4$. Volatiles were stripped on a Schlenk line while warming with a hot water bath, yielding a brown slurry.

EXAMPLE 10

The procedure of Example 7 was repeated, with the differences as follows. The reactor was charged with BuLi (50.34 g, 0.721 mol) and hexane (379.4 g). The reactor jacket was cooled to about −6° C. Diethylamine (55.59 g, 0.760 mol, 105% vs. BuLi) was fed over ~15 minutes while stirring at 200 rpm, with the reaction temperature reaching a high of +10.2° C. The amount of THF used was 112 g (1.55 mol).

Shortly after adding the THF, 1022 g of chlorotitanium diethylamide solution from Example 2 was fed over ~80 minutes while stirring at 200 rpm. Residual chlorotitanium diethylamide solution was washed from the supply bottle with hexane (50 mL). The reaction mixture was stirred overnight at about 20° C. and then volatiles were stripped on a Schlenk line while warming with a water bath.

The resulting brown slurry was combined with that from Example 9 along with hexane (260 g), and the mixture was filtered through a medium porosity glass frit. Volatiles were then stripped from the filtrate, yielding 320 g of red crude $Ti(NEt_2)_4$ having 403 ppm Li and ~2200 ppm hexane. Thus the combined yield of crude $Ti(NEt_2)_4$ from chlorotitanium diethylamides for Examples 9 and 10 was 93%.

EXAMPLE 11

In a nitrogen-purged dry box, a 3-L jacketed reactor equipped with an overhead stirrer and a dropping funnel was charged with BuLi (72.11 g, 1.032 mol) and hexane (625 g). After cooling to ~0° C., diethylamine (90.61 g, 1.105 mol) was added from the dropping funnel over ~40 minutes. The jacket temperature was then increased to 25° C., after which THF (154 g, 2.14 mol) was added, dissolving the $LiNEt_2$.

Chlorotitanium diethylamide solution from Example 3 (1055 g) was fed through a cannula over ~75 minutes. The reaction mixture was stirred at room temperature overnight after which, when the LiCl precipitate was allowed to settle, the supernatant liquid was dark red. NMR analysis confirmed the presence of $Ti(NEt_2)_4$. The mixture was filtered through a medium porosity glass frit, the filtrate was transferred to a 3-L round-bottomed flask. Volatiles were stripped on a Schlenk line, leaving about 350 mL of dark, red-brown material in the flask. Hexane was added, and the mixture was again filtered through a medium porosity frit. The filter cake was washed with hexane (~50 mL), and volatiles were stripped from the filtrate, yielding 213 g of residue consisting of ~4 wt % hexane, 8 wt % diethylamine, and ~88 wt % $Ti(NEt_2)_4$ (187 g, 0.557 mol), corresponding to a titanium recovery of about 81% from chlorotitanium diethylamides.

EXAMPLE 12

The procedure of Example 11 was repeated, with the differences as follows. The reactor was charged with BuLi (77.73 g, 1.113 mol) and hexane (340 g). After cooling to ~0° C., diethylamine (93.15 g, 1.136 mol) was added from the dropping funnel over 90 minutes. The jacket temperature was then increased to 20° C. and THF (155 g, 2.15 mol) was added, dissolving the $LiNEt_2$.

Two different chlorotitanium diethylamide solutions were then introduced: 446 g from Example 2 and 782 g from Example 3. The reaction mixture was stirred at room temperature for two days after which the white solids (LiCl and $LiNEt_2$) were allowed to settle. The supernatant product solution was decanted and its volatile components were stripped on a Schlenk line. Hexane (~300 mL) was added to the resulting slurry, which was then filtered through a medium porosity frit. The filter cake was a white solid. Volatiles were stripped from the brown-red filtrate on a Schlenk line, after which ~200 g of dark brown crude $Ti(NEt_2)_4$ remained, which contained ~1200 ppm hexane.

EXAMPLE 13

The procedure of Example 7 was repeated, with the differences as follows. The reactor was charged with BuLi (82.52 g, 1.288 mol) and hexanes (293 g). After cooling to +11.8° C., diethylamine (110 g, 1.50 mol) was fed portionwise over ~200 minutes, with the temperature increasing to +16.5° C. Tetrahydrofuran (194 g, 2.69 mol) was added and, with vigorous stirring, almost all of the $LiNEt_2$ dissolved.

Chlorotitanium diethylamide solution from Example 4 (1108 g) was fed over 155 minutes while stirring at 199–311 rpm. The reactor's jacket was filled with heat transfer fluid but was "blanked off" to minimize heat removal, and the reaction temperature increased from +22.7° C. to +32.1° C. as the chlorotitanium diethylamides were introduced. The reaction product mixture consisted of white powder dispersed in a greenish-yellow solution.

Volatiles were stripped by heating the reactor's jacket to +45° C. while decreasing the pressure initially to ~367 torr and eventually to ~316 torr over ~165 minutes, during which time the inside pot temperature held steady at +37.5° C. and distillate (b. p. ~+34° C.) was condensed in a ~−7° C. condenser. Additional volatiles were stripped by sweeping nitrogen through the reactor overnight at room temperature while stirring at ~50 rpm, leaving 343 g of slurry (white solid dispersed in green liquid) in the reactor. The slurry was washed from the reactor with hexane (424 g) and filtered through a medium porosity glass frit. Volatiles were stripped on a Schlenk line at room temperature, whereupon additional white precipitate (presumably $LiNEt_2$) formed. After filtering and stripping again, about 275 g of dark, crude $Ti(NEt_2)_4$ were obtained, corresponding to a titanium recovery of ~99% based on chlorotitanium diethylamides.

EXAMPLE 14

The procedure of Example 7 was repeated, with the differences as follows. The reactor was charged with BuLi (63.45 g, 0.991 mol) and hexanes (263 g). After cooling to +11.9° C., diethylamine (89.01 g, 1.217 mol) was fed over 130 minutes, with the temperature increasing to +24.7° C. Tetrahydrofuran (150.5 g, 2.087 mol) was added and, with vigorous stirring, almost all of the $LiNEt_2$ dissolved.

A mixture of chlorotitanium diethylamide solutions, made by combining about 1 gram of filtrate from Example 4 with 1232 g of filtrate from Example 5, was fed over ~1.5 hours while maintaining the reaction temperature at 24.2° C.–24.5° C. and while stirring at 199–311 rpm. Residual chlorotitanium diethylamide solution was washed into the supply bottle with hexane, after which the reaction product mixture was transferred to a 1-gallon bottle, again washing with hexane, yielding 2326 g product mixture. NMR analysis of the product mixture indicated that it contained 0.565 moles of $Ti(NEt_2)_4$, corresponding to a titanium recovery of ~91% based on chlorotitanium amides.

It was noted that the bottom-most part of the chlorotitanium diethylamide solution PTFE feed tube had become black. Also, the inside of the PTFE tube through which the reaction product mixture was removed had also turned black during the transfer, with the first ~4 inches becoming especially dark during the first few seconds of the transfer.

Volatiles were stripped from the product mixture over several days at room temperature, using a Schlenk line protected by a nitrogen-purged glove box. The residue was combined with hexane (168 g), the mixture was filtered through a medium glass frit, and then volatiles were stripped from the filtrate, yielding 189 g of dark red, crude $Ti(NEt_2)_4$, corresponding to 90% titanium recovery from chlorotitanium diethylamides.

EXAMPLE 15

The procedure of Example 7 was repeated, with the differences as follows. The tubes used to feed $HNEt_2$ and chlorotitanium diethylamide solution were made of stainless steel. The reactor was charged with 250 g of ~2.5M BuLi in hexanes (0.9345 moles of neat BuLi), which was washed into the reactor with three portions of hexane (~50 g each). Diethylamine (90.57 g, 1.148 mol) was fed over 95 minutes while stirring at 230 rpm. With the jacket fluid temperature set to 20.0° C., the reaction temperature started at 20.8° C. and steadily increased, reaching a high of 25.9° C. near the end. THF (153 g, 2.12 mol, 227% vs. $LiNEt_2$) was added, and the white $LiNEt_2$ dissolved with vigorous stirring.

A mixture of chlorotitanium diethylamide solutions made by combining 19 grams of filtrate from Example 4 with 1177 g of filtrate from Example 5 was then fed over ~1.5 hours while stirring at 225 rpm. With the jacket temperature set at 20.0° C., the reaction temperature was maintained at 24–25° C. Residual chlorotitanium diethylamide solution was washed in with hexane (4x~35 g). The product mixture was transferred from the reactor through a 0.25 inch outer diameter, 3/16-inch inner diameter PTFE tube. As with Example 12, the inside wall of the tube turned black, with the first few inches becoming darkest, the outside wall of the tube's submerged portion had also turned black. The mixture was washed into a 1-gallon bottle with hexane. A total of 1984 g of product mixture were collected.

After standing at room temperature for two days, the product mixture was transferred portionwise back into the reactor, eventually washing with hexane (2x~500 mL), and volatiles were stripped with the reactor's jacket set at +55° C. while reducing the pressure, until the pressure reached 225 torr. To precipitate leftover $LiNEt_2$ and to remove all of the THF, another ~2 liters of hexane were added and similarly stripped until the pressure eventually reached 109 torr with the nonvolatiles at +53.7° C., after which no THF was detected in the nonvolatile residue by proton NMR.

The nonvolatiles were washed from the reactor with hexane, yielding 638 g of slurry, proton NMR indicated that the slurry contained 210 g of $Ti(NEt_2)_4$, corresponding to quantitative titanium recovery from chlorotitanium amides.

EXAMPLE 16

The procedure of Example 7 was repeated, with the differences as follows. A 3-L reactor was installed in the glove box, with the tubes used to feed $HNEt_2$ and chlorotitanium diethylamide solution made of stainless steel. The reactor was charged with 272 g of ~2.5M BuLi in hexanes (1.008 moles of neat BuLi), which was washed in with hexane (3x~35 g). Diethylamine (89.08 g, 1.218 mol) was fed over 106 minutes while stinting at 205 rpm. With the jacket fluid temperature set to 18.0° C, the reaction temperature started at ~19° C. and steadily increased, reaching a high of ~26° C. THF (184 g, 2.55 mol) was then added, and the white $LiNEt_2$ dissolved with vigorous stirring.

Chlorotitanium diethylamide solution from Example 6 (1209 g) was then fed over ~98 minutes while stirring at 204–206 rpm. With the jacket temperature set at 18.0° C., the reaction temperature started at 18.8° C. and slowly increased. The highest recorded temperature during the reaction was 24.2° C. at 50 minutes. Residual chlorotitanium diethylamide solution was washed in with 2 aliquots of hexane (~75-~100-mL each). NMR analysis indicated quantitative conversion of chlorotitanium diethylamides to $Ti(NEt_2)_4$.

Volatiles were stripped by heating the reactor's jacket to +55° C. while reducing the pressure. Eventually the reactor temperature reached 52.2° C. at 227 torr, with distillate collecting at 35.4° C. To precipitate the leftover $LiEt_2$ and to remove all of the THF, which was complexed to $LiNEt_2$, hexane (802 g) was added after cooling the reactor to room temperature. The hexane and traces of other volatile components (HNEt$_2$ and THF) were then stripped with the jacket temperature set to +55° C. until the pressure was 200 torr with the nonvolatiles at +46° C., and no material was collecting on the ~−7° C. condenser. Another 2 liters of hexane were added and similarly distilled out until the pressure was 176 torr, the nonvolatiles were at +52° C., and no distillate was condensing, after which no THF was detected in the nonvolatiles by proton NMR.

After stirring at room temperature overnight, the nonvolatiles were transferred from the reactor through a PTFE cannula into a ½-gallon bottle, washing the reactor with hexane (3×~150 mL); the cannula did not turn black. The resulting slurry weighed 747 g; proton NMR indicated it contained 215 g of Ti(NEt$_2$)$_4$, corresponding to 98% titanium recovery from chlorotitanium diethylamides.

The 747 g of slurry were combined with the 638 g of slurry from Example 16, and this mixture was filtered through a medium porosity glass frit. The 3-liter reactor was cleaned and then charged with the reddish-brown filtrate. Volatiles were stripped with the reactor's jacket set at +75° C. until the pressure was 225 torr with the nonvolatiles at 61.8° C., after which the jacket temperature was set to +55° C. and stripping was continued until the pressure was 200 torr with the nonvolatiles at +51.1° C.

EXAMPLE 17

After standing at room temperature for three days, a 150-g portion of the, crude Ti(NEt$_2$)$_4$ product from Examples 7 and 8 was added to acetonitrile (300 g) in a round-bottomed flask. The resulting mixture consisted of two phases. The top (acetonitrile) phase was an orange-brown solution; the bottom (Ti(NEt$_2$)$_4$ phase) was an oily yellow solid that occupied about half of the volume after settling. The mixture was cooled in an ice water bath, and then the acetonitrile phase was decanted. Another portion of acetonitrile (~200 mL, ~157 g) was added to the Ti(NEt$_2$)$_4$ phase, and the mixture was stirred while cooling to ~0° C. The mixture was allowed to settle. While the two phases were still present, the Ti(NEt$_2$)$_4$ phase remained well dispersed in the acetonitrile phase, making it impossible to decant much acetonitrile phase without losing some of the Ti(NEt$_2$)$_4$ phase. Several mL of acetonitrile were decanted, and then volatiles were stripped from the remaining mixture on a Schlenk line while warming with a water bath. Toward the end of the volatiles removal, the yellow solids turned into a deep maroon oil which was diluted with hexane (117 g), stirred, and then filtered through a medium porosity glass frit, yielding an orange-yellow solution.

EXAMPLE 18

Acetonitrile (460 g) was added to a 228-g portion of the crude Ti(NEt$_2$)$_4$ product from Examples 7 and 8 that had been standing at room temperature for three days. Two phases formed: an orange-brown upper phase and a lower phase consisting of oily yellow solids. The mixture was cooled to ~0° C. while stirring and then allowed to settle, after which the top phase was easily decanted. This was repeated with more acetonitrile (~200 mL, ~157 g). The oily yellow solid phase settled readily. The second acetonitrile wash phase was decanted, and then the volatiles were stripped from the lower phase on a Schlenk line using a warm water bath. The yellow solids gradually turned into a dark maroon slurry, which became less viscous during the last one-third of the strip. The resulting slurry was diluted with hexane (250 g) and filtered through a medium porosity glass frit, again yielding an orange-yellow solution.

A combined total of about 320 g (0.951 mol) of orange Ti(NEt$_2$)$_4$ was obtained from the acetonitrile treatments of this Example and Example 17.

EXAMPLE 19

Acetonitrile (341 g) was added to the crude Ti(NEt$_2$)$_4$ obtained from Examples 9 and 10. The mixture, which was dark red with a very small amount of orange-red solids, was stirred in an ice-water bath for 30 minutes. Additional acetonitrile (294 g) was added, and the mixture was stirred at ~0° C. for another 20 minutes, whereupon a large amount of yellow-orange solids formed. After allowing the solids to settle, the supernatant (acetonitrile phase), which was a red solution, was decanted. A second acetonitrile portion (139 g) was added, the mixture was cooled to ~0° C. while stirring, then allowed to settle, and then the top phase was decanted.

Volatiles were stripped from the lower phase on a Schlenk line using a warm water bath, leaving a viscous, red-black slurry in the round-bottomed flask. After diluting the slurry with hexanes (~300 g), it was filtered through a medium porosity glass frit, yielding a bright yellow filtrate solution and a dark red filter cake. The filter cake was washed with hexane (~65 g). Most of the hexane was stripped on a Schlenk line using a hot water bath, yielding orange Ti(NEt$_2$)$_4$.

The orange, acetonitrile-treated Ti(NEt$_2$)$_4$ products from this Example, and Examples 17 and 18 were combined and residual volatiles were stripped on a Schlenk line under dynamic vacuum. Hexane and diethylamine levels were monitored over several days. At the end, a total of 641 g (1.90 moles) of final orange Ti(NEt$_2$)$_4$ product were obtained having 0.8 ppm lithium. The titanium recovery for the acetonitrile treatment was ~92%, and the overall yield of purified Ti(NEt$_2$)$_4$ was 81% based on TiCl$_4$ charged.

EXAMPLE 20

The reactor was the same one used for Example 1. It was charged with the dark-brown crude Ti(NEt$_2$)$_4$ product from Example 11, followed by acetonitrile (428 g). No heat evolution was observed, and a three-phase mixture formed: there was a dark-brown lower liquid layer (largely Ti(NEt$_2$)$_4$), an orange-brown-tinged upper liquid layer (largely acetonitrile), and a dark, reddish-brown solid, which was largely concentrated at the interface between the two liquid layers. After stirring for ~1 hour at 23° C., the mixture was allowed to settle for 10 minutes. The top phase, which had become darker than the bottom phase, was decanted, 385 g of top phase were collected. A second acetonitrile portion (475 g) was added to the lower liquid layer (largely Ti(NEt$_2$)$_4$), and the mixture was stirred at 310 rpm for 30 minutes at 23° C. After settling for about 5 minutes, the top phase (475 g) was decanted; it was darker in color than the bottom phase (Ti(NEt$_2$)$_4$), and slightly lighter than the top phase from the first wash. A third acetonitrile wash was done the same way, using 467 g of acetonitrile. After allowing the mixture to settle for 3 minutes, the top phase (470 g) was decanted. The top phase was lighter in color than the lower (Ti(NEt$_2$)$_4$) phase, and much lighter than top phases from the first two acetonitrile washes.

Hexane (430 g) was added to the 3-L reactor, and then volatiles were removed by blowing a stream of nitrogen through the reactor while stirring overnight at 50 rpm at room temperature. The nonvolatile residue looked like overused motor oil. Several grams were removed for analysis, and some was filtered through a 0.2 μm syringe filter, the red Ti(NEt$_2$)$_4$ filtrate contained ~100 ppm diethylamine, ~3300 ppm hexane, and no acetonitrile (by NMR). The remaining product mixture was washed from the reactor with hexane (several washes totaling 530 g) and filtered through a medium porosity glass frit, 670 g of filtrate were collected. The filter cake (~2 g) was a brown mud. A ~7-gram portion of filtrate was removed and volatiles were stripped from it with a stream of nitrogen. The residue (~1.5 g) was $Ti(NEt_2)_4$ containing 0.87 ppm Li and a trace of hexane.

Volatiles were stripped from the remaining ~663 g of filtrate on a Schlenk line while warming with a hot water bath (~49° C. to ~52° C., temperature maintained with a hot plate/stirrer) for about 16 hours. The resulting $Ti(NEt_2)_4$ contained ~1300 ppm diethylamine and ~1700 ppm hexane.

After standing at room temperature overnight, the three acetonitrile phases from the washes were poured into the 3-L reactor which still contained traces of material left after washing the $Ti(NEt_2)_4$ product out with hexane. Volatiles were removed from the acetonitrile washes by blowing a stream of nitrogen through the reactor while stirring for 4 days at 50 rpm at room temperature. The residue (34.3 g, determined later by weighing the reactor before and after washing with hexane) looked like sticky asphalt dispersed in brown oil ($Ti(NEt_2)_4$). As much oily slurry as possible (15.7 g) was syringed out. After standing at room temperature for about a month, the slurry was filtered using several 0.2-μm syringe filters. The orange filtrate was determined by NMR to be $Ti(NEt_2)_4$ with traces of diethylamine, hexane, and unidentified proton-containing contaminants. The $Ti(NEt_2)_4$ product also contained 0.21 ppm Li.

EXAMPLE 21

Acetonitrile (400 g) was added to a portion of crude $Ti(NEt_2)_4$ from Example 12, causing orange-red solids to form. The mixture was cooled in an ice-water bath for ~1 hour while stirring. The solids were then allowed to settle, and the red-black top (acetonitrile) phase was decanted. This was repeated with another 200 mL of acetonitrile. A portion of the bottom phase (48 g) was removed, combined with hexane (48 g), and then filtered through a medium porosity glass frit. The filtrate consisted of a yellow top phase (presumably $Ti(NEt_2)_4$ and hexane) and a red-black bottom phase. After the top phase was decanted, the volatiles were removed from the bottom phase with a nitrogen stream. The $Ti(NEt_2)_4$ obtained had sharp NMR resonances and contained ~2100 ppm hexane, ~240 ppm acetonitrile, and ~630 ppm diethylamine.

Hexane (~300 g) was added to the remaining portion of the bottom phase. The mixture was stirred for a few minutes, then filtered through a medium porosity glass frit. The filter cake was a brownish-red solid, and the filtrate had two layers: a yellow-orange (larger) top phase and a brownish-red oily (smaller) bottom phase. The top phase was decanted. After standing overnight at room temperature, volatiles were stripped from the top phase on a Schlenk line, yielding ~190 g (~0.565 mol) of $Ti(NEt_2)_4$, which contained 0.42 ppm Li. The volatiles were further stripped using a Schlenk line under dynamic vacuum for several days. The product then contained ~100 ppm diethylamine and ~390 ppm hexane.

EXAMPLE 22

The crude $Ti(NEt_2)_4$ from Examples 13, 14, 15, and 16, all of which were black in color, were combined in the 3-liter reactor of the type used in Example 1. Acetonitrile (786 g) was added, and the mixture was stirred at ~500 rpm at 22–23° C. for about 1 hour. The jacket was set to −3° C. and stirring was maintained for about 45 minutes, after which the reaction temperature was +3° C. The stilted was turned off and the mixture allowed to settle for about 20 minutes, and then the top (acetonitrile) phase, which was darker than the $Ti(NEt_2)_4$ phase in the reactor, was decanted with the reaction mixture at +1° C.; 593 g of top phase were removed.

A second acetonitrile wash (786 g) was added with the reactor at +1° C., after which the jacket was set to +30° C. and the stirrer was set to 460 rpm.; the reaction temperature was +28.5° C. after 30 minutes. The jacket was then set to −10° C., and an hour later the reaction temperature was −8° C., after which stirring was stopped and the mixture allowed to settle for about 30 minutes. The second acetonitrile wash, which was darker than the $Ti(NEt_2)_4$ phase in the reactor, was decanted at −8° C.; 757 g of top phase were removed.

A third acetonitrile wash (415 g) was added with the reactor still cold, and then the jacket was set to +30° C. and the stirrer to 510 rpm; the reaction temperature was +28.2° C. after 30 minutes. The jacket was then set to −10° C. and about 30 minutes later the reaction temperature was +1° C., after which stirring was stopped and the mixture allowed to settle for about 20 minutes, during which time the mixture cooled to −5° C. The third acetonitrile wash, which was about the same color as the $Ti(NEt_2)_4$ phase in the reactor, was decanted at −5° C. to −8° C.; 459 g of top phase were removed.

A fourth acetonitrile wash (415 g) was added with the reactor still at −8° C., and then the jacket was set to +30° C. and the stirrer to 493 rpm; the reaction temperature was ~+26° C. after 25 minutes. The jacket was then set to −10° C. and about 30 minutes later the reaction temperature was +0° C., after which stirring was stopped and the mixture allowed to settle for about 20 minutes, during which time the mixture cooled to −5° C. The fourth acetonitrile wash, which was about the same color as the $Ti(NEt_2)_4$ phase in the reactor, was decanted at −5° C.; 439 g of top phase were removed.

The jacket was then set to +25° C. and ~1500 g of hexane were added to the reactor with the stirrer at 200 rpm. Volatiles were then stripped by reducing the pressure. After about 90 minutes, the pot temperature was 21° C., the pressure was 225 torr, and about 175 mL of distillate had been collected (~25 mL of acetonitrile and ~150 mL of hexane). The reactor's jacket was then set to +35° C., and after about 90 minutes an additional ~380 mL of distillate were collected (~60 mL of acetonitrile and ~320 mL of hexane). After another 60 minutes, an additional ~75 mL of distillate were collected and only one liquid phase was condensing, indicating that very little acetonitrile was still present in the pot. After stripping for another four hours, the reaction mixture was transferred from the reactor and filtered through a medium porosity glass frit.

The filtrate solution was red. Proton NMR indicated it was ~40 wt % $Ti(NEt_2)_4$ and ~60 wt % hexane. It was transferred to a clean jacketed, 3-liter reactor of the type used before, and volatiles were stripped until the pressure was 81 torr with the pot at 52.3° C. and the jacket set at +55° C. The stirrer was then set to 357 rpm and nitrogen was blown through the reactor at a rate sufficient to cause nearly violent turbulence while maintaining the pot temperature at +50° C. After blowing nitrogen for about five hours, the $Ti(NEt_2)_4$ product was reddish-orange in color and contained 77 ppm $HNEt_2$, 198 ppm hydrocarbons, and 0.3 ppm Li; 511 g (1.52 moles) of purified $Ti(NEt_2)_4$ were obtained. The titanium recovery for the acetonitrile treatment was about 57%, and the overall yield of purified $Ti(NEt_2)_4$ was about 54%, based on $TiCl_4$.

Compounds referred to by chemical name or formula anywhere in this document, whether referred to in the singular or plural, are identified as they exist prior to coming into contact with another substance referred to by chemical name or chemical type (e.g., another component, a solvent, or etc.). It matters not what preliminary chemical changes, if any, take place in the resulting mixture or solution, as such changes are the natural result of bringing the specified substances together under the conditions specified in this disclosure. Also, even though the claims may refer to substances in the present tense (e.g., "comprises", "is", etc.), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise.

Each and every patent, publication, or commonly-owned patent application referred to in any portion of this specification is incorporated in toto into this disclosure by reference, as if fully set forth herein.

It will also be understood that the terms "substantial" and "substantially" denote that chemical processes ordinarily do not involve absolutes. Thus instead of describing a variable as an absolute, it is far more realistic to describe the variable as being in the substantial vicinity of the expressed variable. For example when describing a stoichiometric quantity it is far more realistic to refer to the quantity as being substantially a stoichiometric quantity since one skilled in the art fully realizes that slight deviations from the absolute stoichiometry would produce no appreciable difference in results. Thus in any and all respects, this document should be read with the application of common sense.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process of preparing dihydrocarbylamido metal compounds, which process comprises:
    a) bringing together, in a liquid reaction medium, at least one metal halide, $MX_4$, where M is titanium, zirconium, or hafnium, and X is a halogen atom, with at least um, and X is a halogen atom, with at least one dihydrocarbylamine, such that a mixture of (i) halometal amides in which the atom ratio of halogen to metal is greater than about 0.1 and less than about 2, and (ii) dihydrocarbylamine hydrohalide is produced;
    b) separating (i) and (ii) from each other; and
    c) bringing together (i) and at least one alkali metal amide, $ANR_2$, where A is an alkali metal, and R is a hydrocarbyl group, in a liquid medium, to produce a product comprised of substantially halogen-free dihydrocarbylamido metal compound.

2. A process as in claim 1 further comprising purifying said product by contacting said product with a nitrile.

3. A process as in claim 2 wherein said nitrile is acetonitrile, propionitrile, butyronitrile, poly(acetonitrile), poly(propionitrile) or poly(butyronitrile).

4. A process as in claim 1 further comprising purifying said product by contacting said product with a nitrile, and wherein said purifying is performed at one or more temperatures in the range of about −30° C. to about 40° C.

5. A process as in claim 1 wherein said at least one dihydrocarbylamine is a single dihydrocarbylamine, and wherein the hydrocarbyl groups of said alkali metal amide correspond to the hydrocarbyl groups of said dihydrocarbylamine.

6. A process as in claim 5 further comprising purifying said product by contacting said product with a nitrile.

7. A process as in claim 6 wherein said nitrile is acetonitrile, propionitrile, butyronitrile, poly(acetonitrile), poly(propionitrile) or poly(butyronitrile).

8. A process as in claim 1 wherein said metal halide, $MX_4$, is titanium tetrachloride.

9. A process as in claim 1 wherein a) is performed at one or more temperatures no higher than about 40° C.

10. A process as in claim 9 further comprising purifying said product by contacting said product with a nitrile.

11. A process as in claim 10 wherein said nitrile is acetonitrile, propionitrile, butyronitrile, poly(acetonitrile), poly(propionitrile) or poly(butyronitrile).

12. A process as in claim 1 wherein in c) is performed at one or more temperatures in the range of about to −15° C. about 40° C.

13. A process as in claim 12 further comprising purifying said product by contacting said product with a nitrile.

14. A process as in claim 13 wherein said nitrile is acetonitrile, propionitrile, butyronitrile, poly(acetonitrile), poly(propionitrile) or poly(butyronitrile).

15. A process as in claim 1 wherein in c) a Lewis base is included in the liquid medium.

16. A process as in claim 15 wherein said Lewis base is at least one ether.

17. A process as in claim 16 wherein said ether is diethyl ether, tetrahydrofuran, or methyltetrahydrofuran.

18. A process as in claim 1 wherein X is a chlorine, bromine, or iodine atom; wherein said at least one dihydrocarbylamine is a single dihydrocarbylamine in which the hydrocarbyl groups each contain, independently, in the range of 1 to about 5 carbon atoms; and wherein the alkali metal amide is a lithium amide in which the hydrocarbyl groups correspond to the hydrocarbyl groups of said dihydrocarbylamine.

19. A process as in claim 1 wherein said metal halide, $MX_4$, is titanium tetrachloride; wherein said at least one dihydrocarbylamine is dimethylamine or diethylamine; and wherein the alkali metal amide is lithium dimethylamide or lithium diethylamide such that the hydrocarbyl groups thereof correspond to the hydrocarbyl groups of said dihydrocarbylamine.

20. A process as in claim 19 further comprising purifying said product by contacting said product with a nitrile.

21. A process as in claim 20 wherein said nitrile is acetonitrile, propionitrile, butyronitrile, poly(acetonitrile), poly(propionitrile) or poly(butyronitrile).

22. A process as in claim 19 wherein in c) at least one ether is present in the liquid medium, and wherein said ether is diethyl ether, tetrahydrofuran, or methyltetrahydrofuran.

23. A process as in claim 1 wherein said metal halide, $MX_4$, is titanium tetrachloride; wherein said at least one dihydrocarbylamine is dimethylamine or diethylamine, wherein the alkali metal amide is lithium dimethylamide or lithium diethylamide such that the hydrocarbyl groups thereof correspond to the hydrocarbyl groups of said dihydrocarbylamine; and wherein in c) at least one ether is present in the liquid medium, and wherein said ether is diethyl ether, tetrahydrofuran, or methyltetrahydrofuran.

24. A process as in claim 23 further comprising purifying said product by contacting said product with a nitrile, and wherein said nitrile is acetonitrile, propionitrile, butyronitrile, poly(acetonitrile), poly(propionitrile) or poly(butyronitrile).

25. A process of preparing dihydrocarbylamido metal compounds, which process comprises reacting at least one alkali metal amide, $ANR_2$, where A is an alkali metal, and R is an hydrocarbyl group, with at least one halometal amide in which the atom ratio of halogen to metal is greater than about 0.1 and less than about 2, where the metal of the halometal amide is titanium, zirconium, or hafnium, in a liquid medium to produce a product comprised of substantially halogen-free dihydrocarbylamido metal compound.

26. A process as in claim 25 further comprising purifying said product by contacting said product with a nitrile.

27. A process as in claim 26 wherein said nitrile is acetonitrile, propionitrile, butyronitrile, poly(acetonitrile), poly(propionitrile) or poly(butyronitrile).

28. A process as in claim 25 further comprising purifying said product by contacting said product with a nitrile, and wherein said purifying is performed at one or more temperatures in the range of about −30 to about 40° C.

29. A process as in claim 25 wherein the hydrocarbyl groups of said alkali metal amide correspond to the hydrocarbyl groups of said halometal amide.

30. A process as in claim 25 wherein said halometal amide is a chlorotitanium amide.

31. A process as in claim 25 wherein said process is performed at one or more temperatures in the range of about −15° C. to about 40° C.

32. A process as in claim 31 further comprising purifying said product by contacting said product with a nitrile.

33. A process as in claim 32 wherein said nitrile is acetonitrile, propionitrile, butyronitrile, poly(acetonitrile), poly(propionitrile) or poly(butyronitrile).

34. A process as in claim 25 wherein a Lewis base is included in the liquid medium.

35. A process as in claim 34 wherein said Lewis base is at least one ether.

36. A process as in claim 35 wherein said ether is diethyl ether, tetrahydrofuran, or methyltetrahydrofuran.

37. A process as in claim 25 wherein the halometal amide is a chlorometal amide, bromometal amide, or iodometal amide, wherein the hydrocarbyl groups of the amide each contain, independently, in the range of 1 to about 5 carbon atoms; and wherein the alkali metal amide is a lithium amide in which the hydrocarbyl groups correspond to the hydrocarbyl groups of said amide.

38. A process as in claim 25 wherein said halometal amide is a chlorotitanium amide; wherein the amides of said halometal amide are dimethylamide or diethylamide; and wherein the alkali metal amide is lithium dimethylamide or lithium diethylamide such that the hydrocarbyl groups thereof correspond to the hydrocarbyl groups of said amides of said halometal amide.

39. A process as in claim 38 further comprising purifying said product by contacting said product with a nitrile.

40. A process as in claim 39 wherein said nitrile is acetonitrile, propionitrile, butyronitrile, poly(acetonitrile), poly(propionitrile) or poly(butyronitrile).

41. A process as in claim 40 wherein a Lewis base is included in the liquid medium, and wherein said Lewis base is at least one ether.

42. A process as in claim 41 wherein said ether is diethyl ether, tetrahydrofuran, or methyltetrahydrofuran.

43. A process as in claim 25 wherein said halometal amide is a chlorotitanium amide; wherein the amides of said halometal amide are dimethylamide or diethylamide; wherein the alkali metal amide is lithium dimethylamide or lithium diethylamide such that the hydrocarbyl groups thereof correspond to the hydrocarbyl groups of said amides of said halometal amide; and wherein at least one ether is present in the liquid medium, and wherein said ether is diethyl ether, tetrahydrofuran, or methyltetrahydrofuran.

44. A process as in claim 43 further comprising purifying said product by contacting said product with a nitrile, and wherein said nitrile is acetonitrile, propionitrile, butyronitrile, poly(acetonitrile), poly(propionitrile) or poly(butyronitrile).

45. A process for purifying a dihydrocarbylamido metal compound, which comprises contacting at least one dihydrocarbylamido metal compound with a nitrile, where the metal of the dihydrocarbylamido compound is titanium, zirconium, or hafnium.

46. A process as in claim 45 wherein said nitrile is acetonitrile, propionitrile, butyronitrile, poly(acetonitrile), poly(propionitrile) or poly(butyronitrile).

47. A process as in claim 45 wherein said purifying is performed at one or more temperatures in the range of about −30° C. to about 40° C.

48. A process as in claim 45 wherein said purifying is performed at one or more temperatures in the range of about −30° C. to about 25° C.

49. A process as in claim 45 wherein said dihydrocarbylamido metal compound is a dihydrocarbylamido titanium compound.

50. A process as in claim 45 wherein the dihydrocarbylamido metal compound is a dihydrocarbylamido titanium compound, and wherein the hydrocarbyl groups of the amide each contain, independently, in the range of 1 to about 5 carbon atoms.

51. A process as in claim 45 wherein said dihydrocarbylamido metal compound is tetrakis(dimethylamido)titanium or tetrakis(diethylamido)titanium.

52. A process as in claim 51 wherein said nitrile is acetonitrile, propionitrile, butyronitrile, poly(acetonitrile), poly(propionitrile) or poly(butyronitrile).

53. A process as in claim 51 wherein said purifying is performed at one or more temperatures in the range of about −30° C. to about 40° C.

54. A process as in claim 51 wherein said purifying is performed at one or more temperatures in the range of about −30° C. to about 25° C.

* * * * *